US010285662B2

United States Patent
Nekovar et al.

(10) Patent No.: US 10,285,662 B2
(45) Date of Patent: May 14, 2019

(54) METHOD FOR ADAPTING AT LEAST ONE RADIATION PARAMETER IN AN X-RAY DEVICE

(71) Applicants: Anton Nekovar, Neunkirchen (DE); Tamás Ujvári, Forchheim (DE)

(72) Inventors: Anton Nekovar, Neunkirchen (DE); Tamás Ujvári, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 200 days.

(21) Appl. No.: 15/341,484

(22) Filed: Nov. 2, 2016

(65) Prior Publication Data

US 2017/0119337 A1 May 4, 2017

(30) Foreign Application Priority Data

Nov. 4, 2015 (DE) .......................... 10 2015 221 638

(51) Int. Cl.
 *A61B 6/00* (2006.01)
(52) U.S. Cl.
 CPC ............ *A61B 6/542* (2013.01); *A61B 6/4035* (2013.01); *A61B 6/465* (2013.01); *A61B 6/469* (2013.01); *A61B 6/486* (2013.01); *A61B 6/5288* (2013.01); *A61B 6/545* (2013.01)
(58) Field of Classification Search
 None
 See application file for complete search history.

(56) References Cited

U.S. PATENT DOCUMENTS

| 5,278,887 A | 1/1994 | Chiu et al. |
| 2011/0075810 A1 | 3/2011 | Sendai |
| 2012/0187312 A1 | 7/2012 | Guez |
| 2012/0235064 A1 | 9/2012 | Guez |
| 2015/0036792 A1 | 2/2015 | Yi et al. |
| 2015/0078516 A1 | 3/2015 | Ohashi et al. |

FOREIGN PATENT DOCUMENTS

DE  102012207623 A1  11/2013

OTHER PUBLICATIONS

German office Action for related German Application No. 10 2015 221 638.1 dated Aug. 21, 2016 with English Translation.

*Primary Examiner* — Hoon K Song
(74) *Attorney, Agent, or Firm* — Lempia Summerfield Katz LLC

(57) ABSTRACT

The embodiments relate to a method for adapting at least one radiation parameter of a beam source in an x-ray device, wherein the beam source is activated according to the radiation parameter for providing x-radiation, wherein, as long as the filter element is not being moved, the radiation parameter is specified based on image data acquired in a transillumination region by the beam detector, wherein at least one interim image is recorded at least partially within a movement interval during which the filter element is moved, after which the radiation parameter is specified independently of the image data of the interim image or after which exclusively image data of the interim image that are acquired in an overlapping region of the beam detector that lies within the transillumination region during the entire recording interval are taken into account in the determination of the radiation parameter.

12 Claims, 3 Drawing Sheets

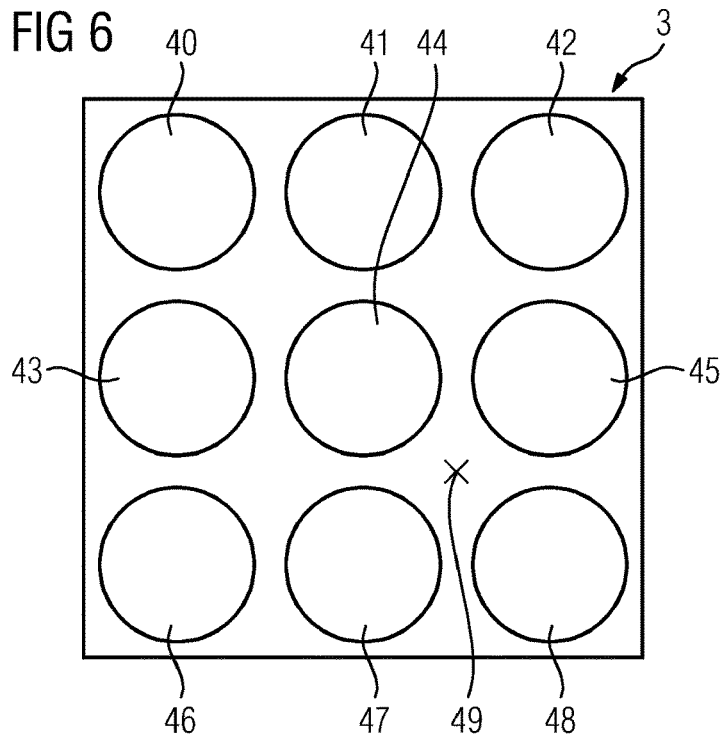
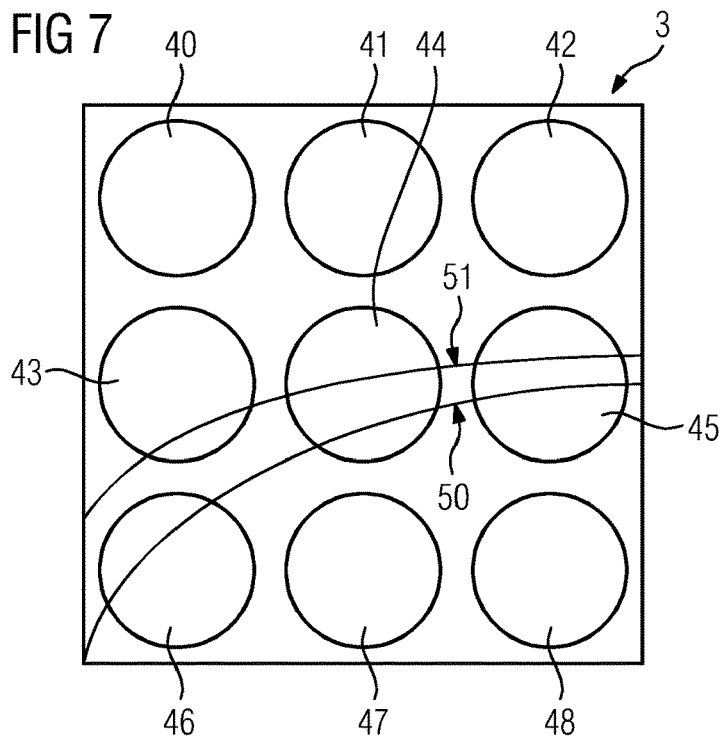

METHOD FOR ADAPTING AT LEAST ONE RADIATION PARAMETER IN AN X-RAY DEVICE

This application claims the benefit of DE 10 2015 221 638.1, filed Nov. 4, 2015, which is hereby incorporated by reference in its entirety.

TECHNICAL FIELD

The embodiments relate to a method for adapting at least one radiation parameter of a beam source in an x-ray device during the recording of a number of transillumination images of an examination object arranged between the beam source and a beam detector, wherein the x-ray device includes a filter element arranged between the beam source and the examination object and has at least one filter section and at least one transillumination section, wherein the x-radiation that passes through the filter section is attenuated more than the x-radiation that passes through the transillumination section, wherein the filter element is movable with respect to the beam source and/or the beam detector, whereby a transillumination region in which an image of the transillumination section is depicted on the beam detector is displaced, wherein the beam source is activated according to the radiation parameter for providing x-radiation. The embodiments also relate to an x-ray device.

BACKGROUND

In an evaluation of x-ray images, only a relatively small region of the image may be relevant. The evaluation of the x-ray images is however greatly facilitated if surrounding regions may also be seen on the x-ray image. It is therefore known to use so-called region-of-interest filters, which allow the x-radiation to pass unhindered in a region of interest and attenuate the x-radiation in regions adjacent to this region. An adaptation of the brightness and an optional filtering in the course of the evaluation make it possible to display the region of interest with high resolution and little noise, while the regions adjacent thereto are displayed with lower quality, which however is sufficient to provide a context for the region of interest.

In the examination of objects with x-radiation, (e.g., in the case of medical use), it is desirable to reduce the radiation exposure of the examination object and nevertheless achieve a required image quality. It is known for this purpose to control a radiation dose emitted onto the examination object in dependence on a previously acquired x-ray image. Control may take place, for example, in dependence on an image brightness, a contrast, or a signal-to-noise ratio. If such a method is applied when using the filters described above, it may be problematic that the image quality in the region of the image that is covered by the filter section is reduced, as a result of which the dose control is adversely affected, which may lead to an unnecessary increase in the dose and/or to an overexposure in the transillumination section. Moreover, the transmission behavior of the filter material often differs significantly from the transmission behavior of the material of the examination object. In particular, when there is a movement of the filter for displacing a region of interest, this may lead to control oscillations or to other instabilities of the dose control. This may on the one hand increase the radiation exposure of the examination object and on the other hand reduce the image quality of transillumination images.

SUMMARY AND DESCRIPTION

The scope of the present invention is defined solely by the appended claims and is not affected to any degree by the statements within this summary. The present embodiments may obviate one or more of the drawbacks or limitations in the related art.

The embodiments are based on the object of providing a method for adapting a radiation parameter in an x-ray device that improves a dynamic optimization of the image quality with the lowest possible radiation dose and with use of a filter element, in particular, a quickly moved filter element, for the attenuation of radiation.

The object is achieved by a method of the type mentioned at the beginning, wherein, as long as the filter element is not being moved, the radiation parameter is specified in dependence on image data of the last-recorded of the transillumination images acquired in the transillumination region by the beam detector, wherein at least one interim image is recorded as one of the transillumination images during a recording interval that lies at least partially within a movement interval during which the filter element is moved from a starting position into an end position, after which the radiation parameter is specified independently of the image data of the interim image or after which exclusively image data of the interim image that are acquired in an overlapping region of the beam detector that lies within the transillumination region during the entire recording interval are taken into account in the determination of the radiation parameter.

The provision of x-radiation may take place by emitting an electron beam onto an x-ray target. A radiation intensity of the emitted x-radiation and/or an acceleration voltage for the electron beam and/or a charge transported in a pulse of the electron beam and/or a length of the pulse over time and/or an attenuation parameter may be specified as the radiation parameter. The attenuation parameter may describe the number and/or the thickness of copper filters for the absorption of low-energy x-radiation that are to be introduced into the beam path by an actuator.

The method avoids carrying out control in dependence on those image data of transillumination images that are acquired in regions of the beam detector in which the incident x-radiation is attenuated by a filter section in at least one period of the recording interval. As a result, the initially mentioned possible increases in dose, instabilities or control oscillations of the dose control are avoided and a high image quality may be achieved, in particular, for the transillumination region, with nevertheless low radiation exposure of an examination object.

The filter element may be designed in such a way that the x-radiation passing through the transillumination section is not attenuated. For example, the transillumination section may be designed as a clearance in the filter element through which x-radiation may pass unhindered. The attenuation in the filter section may vary, a continuous transition of the strength of the attenuation from the transillumination section into the filter section being possible, for example, by a material thickness increasing in a wedge-shaped manner.

The transillumination images may be projection images that are recorded in an x-ray device for the recording of two-dimensional image data. The transillumination images may also be individual images of a 3D imaging process, for example, in a CT scanner.

The beam detector may be designed for the spatially resolved acquisition of a radiation intensity occurring on the beam detector. It may be designed as a two-dimensional array of detector elements.

A movement of the filter element may take place in the method by an actuator of the x-ray device. The control of the actuator may take place automatically or in dependence on user inputs. The x-ray device may include a control device, which serves for specifying the radiation parameter and for correspondingly activating the beam source and/or activating the actuator for moving the filter element.

The radiation parameter may be specified during the movement interval in dependence on image data of the last of the transillumination images recorded before the beginning of the movement interval acquired in the transillumination region by the beam detector. The specifying of the radiation parameter may take place here additionally in dependence on the image data of the interim image or independently of these image data.

The movement from the starting point to the end point may be stopped during the recording interval, after which the radiation parameter is specified in dependence on image data of the interim image acquired by the beam detector in the transillumination region corresponding to the overlapping region. The movement of the filter element and the recording of the interim image or the interim images are synchronized in such a way that the transillumination region is not displaced during the recording interval. The overlapping region is therefore identical to the transillumination region.

The radiation parameter in the movement interval may be specified in dependence on a position of the filter element. Such a dependence is advantageous if the specifying of the radiation parameter takes place independently of the image data of the interim image, but the various dependences may also be used in a combined manner. It may be known or have been ascertained by previous measurements that different radiation parameters are advantageous for different positions of the filter element. This may be caused by properties of the examination object or by a measuring geometry of the x-ray device. Such dependences may be taken into account by an adaptation of the radiation parameter in dependence on the position of the filter element, and consequently of the transillumination region within the image region. The dependence of the radiation parameter on the position may be defined by a mathematical relationship, but it is also possible to specify for a number of specified positions a desired radiation parameter or variable on which the desired radiation parameter at one position depends. A desired radiation parameter, or a variable on which the desired radiation parameter depends, for the position at the particular time may be determined, for example, by it being interpolated from corresponding variables for specified positions lying close to the position at the particular time.

Reference images on the basis of which the radiation parameter is specified during the movement interval in dependence on image data of at least one of the reference images may be recorded for a number of reference positions of the filter element with the filter element stationary. It is not necessary for this that the entire reference image is stored or evaluated for the determination of the radiation parameter. For example, for each of the reference images there may be determined one or more reference variables on the basis of which the radiation parameter is specified in dependence on the reference variable or the reference variables of at least one of the reference images. The radiation parameter may be specified in dependence on one of the reference images that is assigned to a reference position that lies closest to the position at the particular time of the filter element. Alternatively, a number of reference images may be evaluated, for example, by interpolating between the reference images or their assigned reference variables. This may involve taking into account, for example, all of the reference images of which the reference positions lie adjacent to the momentary actual position of the filter element.

The specifying of the radiation parameter in the movement interval may take place in dependence on at least one parameter of the examination object that changes during the movement interval. This is advantageous particularly whenever the examination object is a living examination object. In this case, a vital parameter of the examination object, for example, a parameter derived from an electrocardiogram or a parameter of the respiration, (in particular, a respiratory phase), may be acquired as the parameter or one of the parameters. The parameter of the examination object may be acquired by sensors. In addition, or alternatively, transillumination images or a directly preceding transillumination image, which may also be an interim image, may be evaluated in order to ascertain a parameter of the examination object, in dependence on which the radiation parameter is specified. For example, the position of a diaphragm in the image data may be detected in order to adapt the radiation parameter in dependence on a respiratory phase.

At each of the reference positions, there may be acquired a number of the reference images, which are assigned to different reference values of the parameter, on the basis of which the radiation parameter is specified during the movement interval in dependence on image data of at least one of the reference images that is selected in dependence on the parameter. As previously explained, it is possible not to evaluate the reference images themselves but reference variables derived from them. The reference image of which the reference value for the parameter and of which the reference position come closest to the actual position of the filter element and the actual value of the parameter may be evaluated. However, it is also possible, as previously described, to interpolate between a number of the reference images or between a number of reference variables derived from these reference images.

In the method, it is possible that the specified radiation parameter is specified as constant during the movement interval.

When acquiring a user input determining a relevant region of the examination object, the filter element may be moved into the end position that is determined in dependence on the user input and in which the region depicted in the transillumination region includes the relevant region. The movement may take place by an actuator of the x-ray device, the actuator being activated by the control device. The user input may be acquired by a viewing direction of the user being acquired by an acquisition device of the x-ray device. For example, that region at which a user is looking in a previously acquired transillumination image may be interpreted as the relevant region. By such an eye-tracking method in the case of a real-time display of x-ray data, it may be achieved that the region at which a user is directing their attention is depicted with particularly high contrast and clarity, by the filter element being moved in such a way that no attenuation of the radiation takes place in this region. Alternatively, it would be possible to acquire a user input by an operator element, such as a touchscreen.

When using eye tracking, it is advantageous if the end position is reached very quickly, so that a region of interest to a user may be displayed with high quality to the user without a notable delay. In order to achieve this, the filter element is moved relatively quickly, so that the transillumination regions in successively following transillumination images are strongly displaced with respect to one another.

Specifically in these cases, the adaptation of the radiation parameter is advantageous, since otherwise unnecessary overexposures, underexposures, instabilities, or oscillations of the radiation intensity may occur.

Advantageously, an image display of the last-recorded of the transillumination images may be displayed by a display device, wherein the image display includes image data acquired in the transillumination region and image data of a filter region in which an image of at least part of the filter section is depicted. It is possible here that a preprocessing of the image data takes place before the display, wherein in particular the brightness and/or the contrast of the image data may be adapted in the filter region and/or a temporal and/or spatial filtering may be performed in the filter region, in order to make the display in the filter region similar to the display in the transillumination region. This procedure achieves the effect that the particularly relevant transillumination region is displayed to a user with low noise and high contrast, a context for the transillumination region being provided at the same time by the display of the filter region. A corresponding display also makes it possible to select a relevant region.

Apart from the method, the embodiments relate to an x-ray device, including a beam source; a beam detector; a filter element that is arranged between the beam source and an examination volume for the recording of an examination object to be transilluminated and has at least one filter section and at least one transillumination section; a control device; and at least one actuator for moving the filter element with respect to the beam source and/or the beam detector, wherein the filter section is designed to attenuate x-radiation passing through it more than x-radiation passing through the transillumination section, the control device being designed for carrying out the method. The control device serves for controlling the beam source and optionally for controlling the actuator. It may be designed for acquiring image data from the beam detector and for processing the image data for specifying the radiation parameter and/or for providing measurement data. In a development of the x-ray device, the control device may also activate a display device for displaying the transillumination images and/or acquire sensor data from sensor devices in order to ascertain a viewing direction of a user.

Features, advantages and properties that are disclosed with respect to the method or the x-ray device may be respectively transferred correspondingly to the other subject matter.

BRIEF DESCRIPTION OF THE DRAWINGS

Further advantages and details are shown by the following exemplary embodiments and the associated drawings, in which schematically:

FIGS. 6 and 7 depict the use of reference images in various exemplary embodiments of the method.

DETAILED DESCRIPTION

Figure 1:
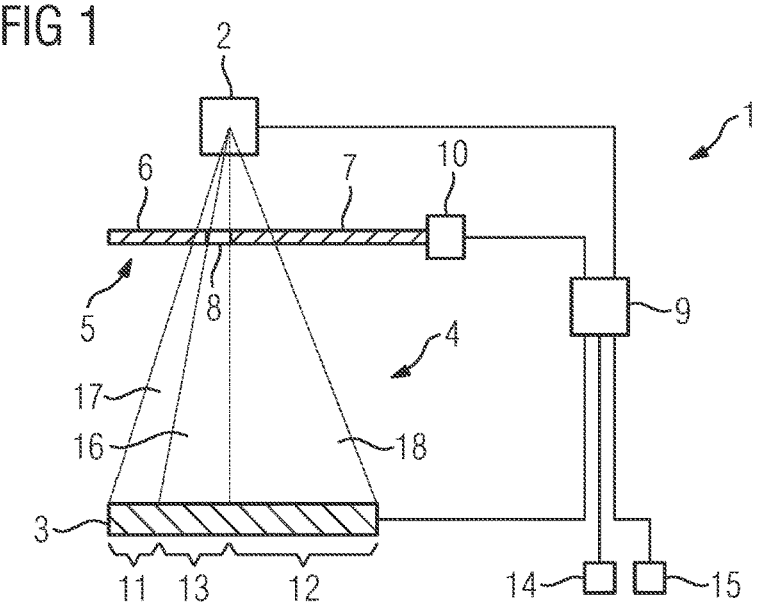
FIG. 1 depicts an exemplary embodiment of an x-ray device.

FIG. 1 depicts an x-ray device 1, including a beam source 2, a beam detector 3, and a filter element 5 arranged between the beam source 2 and an examination volume 4. The filter element 5 has two filter sections 6, 7 and a transillumination section 8, the filter sections 6, 7 being designed in such a way that x-radiation that passes through them is attenuated more than x-radiation that passes through the transillumination section 8. The x-ray device 1 also has an actuator 10 in order to displace the filter element 5.

Image data are acquired by the beam detector 3 in three regions, specifically in the filter regions 11, 12, in which in each case images of the filter sections 6, 7 are at least partially geometrically depicted, and in the transillumination region 13, in which an image of the transillumination section 8 is geometrically depicted. Consequently, the transillumination section 13 depicts a relevant region 16 of the examination volume 4 or of the examination object that is transilluminated with a higher radiation dose in comparison with the further regions 17, 18 of the examination volume 4. Therefore, a higher contrast and/or a higher signal-to-noise ratio may be achieved in the transillumination region 13 than in the filter regions 11, 12.

Figure 2:
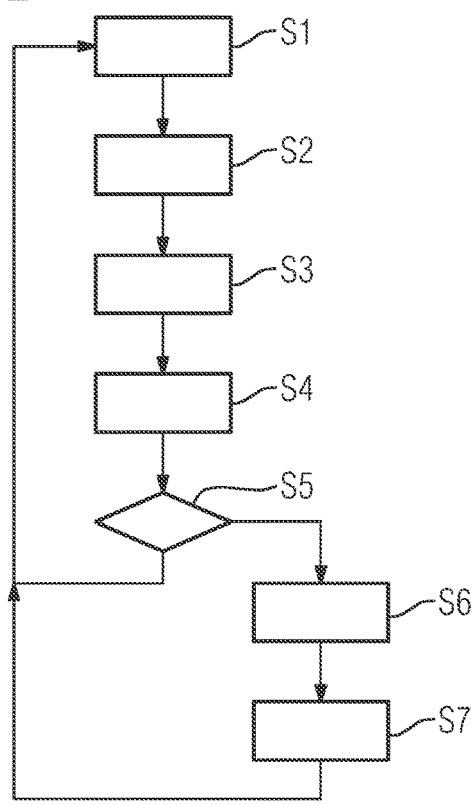
FIG. 2 depicts a flow diagram of an exemplary embodiment of the method.

The recording of a number of transillumination images is explained below with reference to FIG. 2. In act S1, an transillumination image is recorded. For this purpose, the control device 9 activates the beam source 2, in order to emit a radiation pulse. The x-rays emitted by the beam source 2 pass through the filter element 5 and the examination volume 4 with an examination object arranged therein and impinge on the beam detector 3. The x-rays are thereby attenuated on the one hand by the filter regions 6, 7 of the filter element 5 and on the other hand by the examination object. The beam detector 3 includes pixels arranged in the manner of a matrix and respectively pick up an incident radiation intensity and provide it as image data to the control device 9.

In act S2, a radiation parameter according to which the beam source 2 is to be activated for emitting x-radiation, is determined by the control device 9 in dependence on the image data. With a filter element that is not moved, it is primarily intended for the image quality in the relevant region 16 to be improved, e.g., the image quality for the image data acquired in the transillumination region 13. Therefore, the image data that were acquired in the transillumination region 13 are taken into account in the determination of the radiation parameter. The determination of the radiation parameter may take place in the form of a closed-loop control, for example, a proportional-integral control. An average or maximum acquired radiation intensity in the transillumination region 13, a contrast within the transillumination region 13, a signal-to-noise ratio in the transillumination region 13, or a variable derived from these and/or further variables may be used as the input variable. Subsequently, the control device 9 activates the beam source 2 according to the radiation parameter for emitting the x-radiation. Methods for specifying a radiation parameter in dependence on acquired image data are known in the prior art and consequently do not need to be explained in detail.

In act S3, the control device 9 ascertains an image display from the image data provided and activates a display device 14, in order to display these image data. In the preparation of the image display, it is taken into account that the x-radiation that is incident on the detector 3 in the filter regions 11, 12 is attenuated more by the filter element 5 than the x-radiation that is incident on the detector 3 in the transillumination region 13. In order to achieve a clear image display, the image data acquired in the filter regions 11, 12 are preprocessed by the control device 9 in order to adapt the brightness and/or the contrast to the image data acquired in the transillumination region 13. In addition, the image data from the filter regions 11, 12 may be spatially and/or temporally filtered, in order to adapt a signal-to-noise ratio to the image data that were acquired in the transillumination region 13.

In act S4, user inputs by which a user may specify a relevant region 16 of the examination object or the examination volume 4 for which the image quality is to be optimized are acquired. For this purpose, a viewing direction of a user, and consequently the region of the display device 14 at which the user is looking, is ascertained by an acquisition device 15, which may for example include a number of cameras. Since the image display displayed on the display device 14 depicts the entire examination volume, each part of the examination volume 4 may be selected as a relevant region 16 by the user correspondingly directing its view. In alternative exemplary embodiments, the display device 14 may be designed as a touchscreen, whereby a relevant region 16 would be selectable by touch.

In act S5, it is checked whether the relevant region 16 chosen by the user is already depicted on the transillumination region 13 of the beam detector 3. In this case, the relevant region 16 is already depicted with x-rays that are not attenuated by the filter element 5, for which reason the method may be continued with act S1, and consequently with the acquisition of a further transillumination image. If, however, the relevant region 16 is completely or partially depicted within the filter regions 11, 12, the filter element 5 may thus be moved by the actuator 10 in order to displace the transillumination region 13 in such a way that the relevant region 16 is depicted on it.

Figure 3:
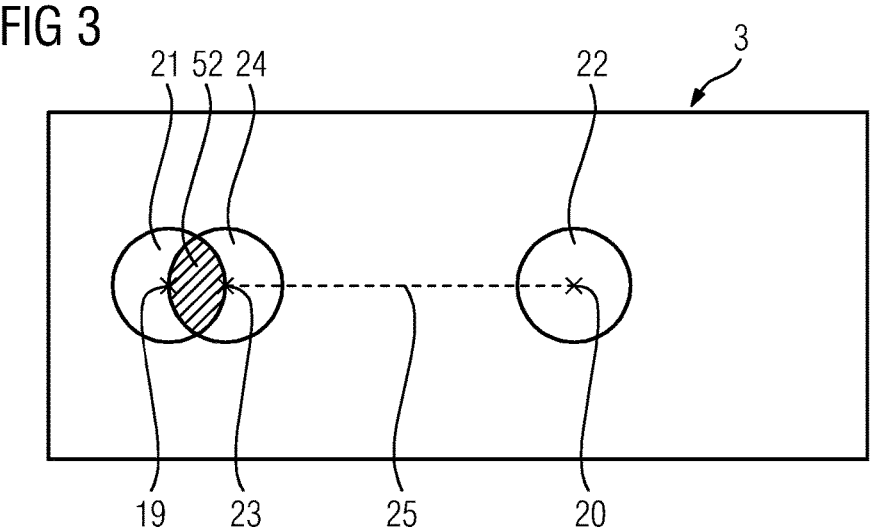
FIG. 3 depicts a movement of a transillumination region during a movement interval in an exemplary embodiment of the method.

For this purpose, the control device 9 determines in act S6 an end position into which the filter element 5 may be brought by the actuator 10. In act S7, the actuator 10 is activated by the control device 9 in a movement interval in such a way that the filter element is moved from its starting position into the previously determined end position. An example of a resultant movement of the transillumination section 13 is represented in FIG. 3. The starting position 19 and the end position 20 are represented here as dots, which correspond to a projection of the center of the transillumination section 8 onto the beam detector 3. The transillumination region 21 results from the starting position 19 of the filter element 5 and the transillumination region 22 results from the end position 20 of the filter element 5.

It may be desired during a movement interval that the filter element 5 is moved from the starting position 19 to the end position 20 to record one or more interim images. In particular, transillumination images may be recorded with a fixed repetition frequency irrespective of whether the filter element 5 is moved or not. By way of example, a position 23 of the filter element with an associated transillumination region 24 for the recording of a single interim image is represented in FIG. 3. Further potential recordings are indicated by the dotted line 25.

The assignment of a fixed position 23 of the filter element 5 to an interim image that is recorded during the movement interval may be an exemplary situation, at least if the movement takes place continuously. In an actual x-ray device, an interim image is recorded during a specific recording interval, the length of the recording interval corresponding substantially to the length of a radiation pulse emitted by the beam source 2. If high rates of movement for the filter element 5 are to be made possible, the movement during a recording interval is no longer negligible. Parts of the image data recorded in regions that lay within a filter region 11, 12 for part of the recording interval and lay in a transillumination region 13, 21, 22, 24 for part of the recording interval. If a specification of the radiation parameter takes place in dependence on such image data, this may lead to instabilities, and, in particular, oscillations of the radiation intensity, as a result of the often different absorption behavior of the filter regions 6, 7 in relation to the examination object. Various possibilities for specifying the radiation parameter in act S7, (e.g., during the movement interval), that avoid such instabilities are discussed below with reference to FIG. 4 and FIG. 5.

Figure 4:
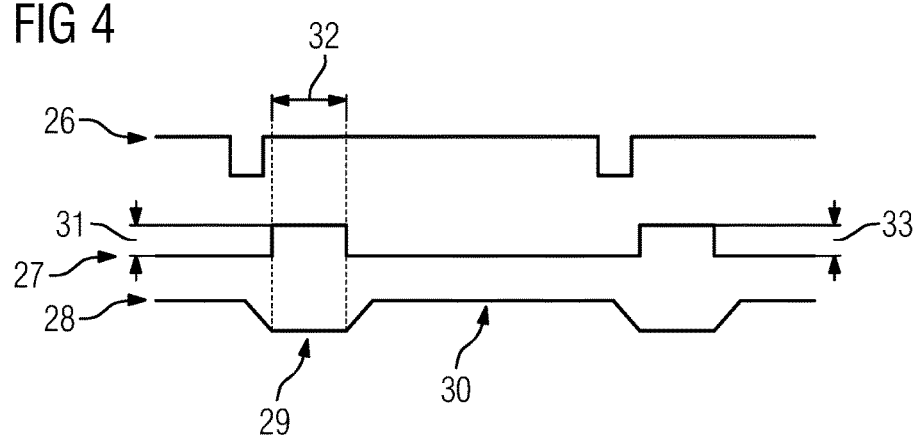
FIGS. 4 and 5 depict control signals for various components of an x-ray device in various exemplary embodiments of the method.

In the exemplary embodiment depicted in FIG. 4, the movement from the starting point 19 to the end point 20 is in each case stopped during the recording interval. In FIG. 4, three control signals 26, 27, 28, provided by the control device 9 for the actuator 10, the radiation source 2, and the beam detector 3, are represented. The control signal 28 specifies a rate of movement of the filter element 5. At a zero point 29 of the control signal 28, the actuator 10 is stationary and the filter element 5 is not moved. At a maximum point 30 of the control signal 28, the actuator 10 is operated at a specified maximum rate, so that the filter element 5 is displaced. The control signal 27 is fed to the beam source 2. The amplitude 31 of the control signal 27 correlates with the radiation intensity emitted by the beam source 2 and is intended to be specified as a radiation parameter. The control signal 26 is a gate signal for the beam detector 3, by which the individual transillumination images are separated.

For the recording of a transillumination image during the movement interval, the control signal 28 is continuously lowered to zero by the control device 9 in order to stop the movement of the filter element 5. The recording readiness of the beam detector 3 is established by the control signal 26 and the beam source 2 is subsequently activated by a control signal 27 in the form of a pulse with the amplitude 31 in order to trigger a beam pulse with the specified length and intensity. After the end of the beam pulse, the actuator 10 is activated by the control signal 28 in order to resume the movement of the filter element 5.

Subsequently, the radiation parameter for the recording of the next transillumination image, (e.g., the amplitude 33 of the next pulse of the control signal 27), is specified in dependence on the image data of the previously recorded transillumination image or interim image acquired in the transillumination region 13, 21, 22, 24.

The described procedure makes possible on the one hand a robust control of the radiation intensity and on the other hand a relatively easy adaptation of the display of the image data from the transillumination region 13, 21, 22, 24 and the image data from the filter regions 11, 12 to one another, since there are no regions of the image in which an attenuation of the incident x-radiation by the filter regions 6, 7 only took place during part of the recording interval 32.

Figure 5:
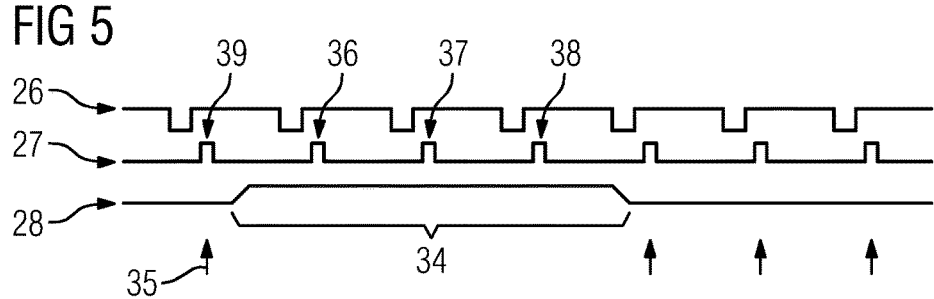

FIG. 5 depicts the control signals 26, 27, 28 for controlling the actuator 10, the beam source 2 and the beam detector 3 in an alternative exemplary embodiment for the adaptation of a radiation parameter in the x-ray device 1. The main difference from the exemplary embodiment represented in FIG. 4 is that the control signal 28 for the actuator 10 has a high value during the entire movement interval 34, e.g., the actuator is active during the entire movement interval 34. Therefore, the filter element 5 moves at a substantially constant rate during the movement interval 34. As may be seen from the control signals 27 and 26 for the beam source 2 and the beam detector 3, respectively, a number of interim images 36, 37, 38 are recorded during the movement interval 34. The arrows 35 mark those transillumination images in dependence on the image data of which a radiation parameter is specified for subsequent radiation pulses.

As shown, the radiation parameter is specified in the movement interval 34 independently of the image data of the interim images 36, 37, 38. In one example, the specified radiation parameter may be constant in the movement interval 34, e.g., the control of the radiation parameter is stopped. The radiation parameter may be specified in dependence on image data of the last of the transillumination images 39 recorded before the beginning of the movement interval 34 acquired in the transillumination region 13, 21, 22, 24 by the beam detector 3. Alternatively, or in addition, the radiation parameter may be controlled in an open-loop or closed-loop manner in the movement interval 34 in dependence on further parameters. Examples of this will be discussed further with reference to FIG. 6 and FIG. 7.

Alternatively, it would also be possible also to use image data of the interim images 36, 37, 38 for adapting the radiation parameter of the respectively following radiation pulse. In this case, exclusively those image data of the interim images 36, 37, 38 that are acquired in an overlapping region of the beam detector that lies within the transillumination region 13, 21, 22, 24 during the entire recording interval 32 may be used in each case. An example of such an overlapping region is represented in FIG. 3 as overlapping region 52. In the overlapping region 52, exclusively x-rays that have not been attenuated by the filter sections 6, 7 are detected during the recording interval. Therefore, with exclusive use of these image data, instabilities of the adaptation of the radiation parameter are avoided.

It is also possible to combine the possibilities for adapting the radiation parameter that are explained with reference to FIG. 5. It is for example, possible that different lengths of recording intervals or different lengths of radiation pulses, are used in the x-ray device 1 and/or the filter element 5 may be moved at different rates by the actuator 10. The size of the overlapping region 52 depends on the length of the recording interval and on the rate of movement of the filter element 5. If the overlapping region has a specified minimum size, the image data of the interim images 36, 37, 38 assigned to this region may be used for adapting the radiation parameter. Otherwise, the adaptation of the radiation parameter may take place independently of the image data of the interim images 36, 37, 38.

FIGS. 6 and 7 depict two exemplary embodiments for the use of reference images recorded at specified reference positions of the filter element for adapting the radiation parameter. It is possible to use the described procedure for adapting the radiation parameter during the movement interval 34 if, as described in FIG. 5, no account of the image data of the interim images 36, 37, 38 is taken during this interval. The described procedure may however also be used in addition to the evaluation of image data for adapting the radiation parameter in order to adapt the radiation parameter in dependence on a number of factors.

FIG. 6 schematically depicts the recording of reference images for a number of reference positions of the filter element, the reference images 40 to 48 being represented by the position of their transillumination regions on the detector device 3. The reference images are respectively recorded with a stationary filter element 5 on the examination object to be examined. For each of the reference images 40 to 48, a desired radiation parameter for the corresponding reference image 40 to 48 or the corresponding reference position is ascertained in dependence on the image data acquired in the respective transillumination region.

If in the further course of the method a transillumination image or an interim image, is to be recorded at a specific actual position 49 of the filter element 5, the radiation parameter of the radiation pulse that is used is specified in dependence on the image data of at least one of the reference images 40 to 48. The radiation parameter may be determined by it being interpolated from the desired radiation parameters previously ascertained for the reference positions of the filter element adjacent to the actual position 49. If the filter element is for example at the actual position 49, which lies centrally between the reference positions of the reference images 44, 45, 47, 48, the radiation parameter may be determined from the desired radiation parameters of the reference images 44, 45, 47, 48 by averaging.

FIG. 7 depicts a continuation of the exemplary embodiment shown in FIG. 4, the specifying of the radiation parameter taking place additionally in dependence on a parameter of the examination object, specifically a respiratory phase. In the example shown, a recording of transillumination images of the chest takes place, the region of the diaphragm being depicted. By way of example, a position 50 of the diaphragm that corresponds to full inhalation and a position 51 of the diaphragm that corresponds to full exhalation are presented. The varying position of the diaphragm over time makes it advantageous to use radiation parameters that vary over time. Therefore, each of the reference images 40 to 48 is recorded once when the examination object has fully inhaled and once when the examination object has fully exhaled. The respiratory phase of the examination object is picked up by a breathing sensor. In addition to the interpolation between the reference images assigned to the various positions, as was explained in relation to FIG. 6, in the exemplary embodiment according to FIG. 7 interpolation is also performed between the reference images that are assigned to the various respiratory phases.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for adapting at least one radiation parameter of a beam source in an x-ray device during a recording of a number of transillumination images of an examination object arranged between the beam source and a beam detector, the x-ray device having a filter element arranged between the beam source and the examination object and having at least one filter section and at least one transillumination section, wherein x-radiation that passes through the at least one filter section is attenuated more than x-radiation that passes through the at least one transillumination section, and wherein the filter element is movable with respect to the beam source, the beam detector, or the beam source and the beam detector whereby a transillumination region in which an image of the at least one transillumination section is depicted on the beam detector is displaced, the method comprising:

activating the beam source according to the at least one radiation parameter for providing x-radiation, wherein, as long as the filter element is not being moved, the at least one radiation parameter is specified based on image data of a last-recorded image of the transillumination images acquired in the transillumination region by the beam detector;

recording at least one interim image as one image of the transillumination images during a recording interval that lies at least partially within a movement interval during which the filter element is moved from a starting position into an end position; and specifying, after the recording of the at least one interim image, the at least one radiation parameter independently of image data of the at least one interim image or after which exclusively image data of the at least one interim image that are acquired in an overlapping region of the beam detector that lies within the transillumination region during an entire recording interval are taken into account in the determination of the at least one radiation parameter.

2. The method of claim 1, wherein the at least one radiation parameter is specified during the movement interval based on image data of a last of the transillumination images recorded before the beginning of the movement interval acquired in the transillumination region by the beam detector.

3. The method of claim 1, wherein the movement from the starting point to the end point is stopped during the recording interval, after which the at least one radiation parameter is specified based on image data of the interim image acquired by the beam detector in the transillumination region corresponding to the overlapping region.

4. The method of claim 1, wherein the at least one radiation parameter in the movement interval is specified based on a position of the filter element.

5. The method of claim 1, wherein reference images based on which the at least one radiation parameter is specified during the movement interval based on image data of at least one of the reference images are recorded for a number of reference positions of the filter element with the filter element stationary.

6. The method of claim 1, wherein the specifying of the at least one radiation parameter in the movement interval takes place based on at least one parameter of the examination object that changes during the movement interval.

7. The method of claim 6, wherein a number of the reference images are acquired at each reference position, wherein the reference images are assigned to different reference values of the at least one parameter, based on which the at least one radiation parameter is specified during the movement interval based on image data of at least one of the reference images that is selected based on the at least one parameter.

8. The method of claim 1, wherein the at least one radiation parameter is specified as constant during the movement interval.

9. The method of claim 1, wherein, when acquiring a user input determining a relevant region of the examination object, the filter element is moved into the end position determined based on the user input and in which the region depicted in the transillumination region includes the relevant region.

10. The method of claim 9, wherein the user input is acquired by a viewing direction of the user being acquired by an acquisition device of the x-ray device.

11. The method of claim 1, wherein an image display of the last-recorded image of the transillumination images is displayed by a display device, wherein the image display comprises image data acquired in the transillumination region and image data of a filter region in which an image of at least part of the at least one filter section is depicted.

12. An x-ray device, comprising:
a beam source;
a beam detector;
a filter element arranged between the beam source and an examination volume, wherein the filter element is configured to record a number of transillumination images of an examination object arranged between the beam source and the beam detector, wherein the filter element has at least one filter section and at least one transillumination section;
a control device; and
at least one actuator for moving the filter element with respect to the beam source, the beam detector, or the beam source and beam detector, wherein the at least one filter section is configured to attenuate x-radiation passing through the at least one filter section more than x-radiation passing through the at least one transillumination section,
wherein the filter element is movable with respect to the beam source, the beam detector, or the beam source and the beam detector whereby a transillumination region in which an image of the at least one transillumination section is depicted on the beam detector is displaced,
wherein the beam source is configured to be activated according to at least one radiation parameter for providing x-radiation, wherein, as long as the filter element is not being moved, the at least one radiation parameter is specified based on image data of a last-recorded image of transillumination images acquired in the transillumination region by the beam detector,
wherein at least one interim image is configured to be recorded as one image of the transillumination images during a recording interval that lies at least partially within a movement interval during which the filter element is moved from a starting position into an end position, and
wherein the at least one radiation parameter is configured to be specified, after the recording, independently of image data of the at least one interim image or after which exclusively image data of the at least one interim image acquired in an overlapping region of the beam detector that lies within the transillumination region during an entire recording interval are taken into account in the determination of the at least one radiation parameter.

* * * * *